(12) United States Patent
Choi

(10) Patent No.: US 8,828,542 B2
(45) Date of Patent: Sep. 9, 2014

(54) NANOPARTICLES

(75) Inventor: Dong Hoon Choi, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 505 days.

(21) Appl. No.: 12/713,443

(22) Filed: Feb. 26, 2010

(65) Prior Publication Data

US 2011/0213046 A1    Sep. 1, 2011

(51) Int. Cl.
| | |
|---|---|
| C08G 79/00 | (2006.01) |
| C07K 2/00 | (2006.01) |
| B32B 15/02 | (2006.01) |
| C07K 1/04 | (2006.01) |
| B82Y 5/00 | (2011.01) |

(52) U.S. Cl.
CPC .. *C07K 1/042* (2013.01); *B82Y 5/00* (2013.01)
USPC ........ 428/402.2; 521/124; 530/345; 530/400; 530/334; 528/9; 428/336; 428/367; 428/368; 428/402.1

(58) Field of Classification Search
USPC ............... 521/124; 528/9; 530/345, 400, 334; 536/22.1; 428/336, 368, 367, 457, 702, 428/411.1, 402–402.24, 407; 252/62.51, 55
See application file for complete search history.

(56) References Cited

U.S. PATENT DOCUMENTS

| | | | |
|---|---|---|---|
| 2005/0092428 A1* | 5/2005 | Crivello ................. | 156/273.3 |
| 2009/0053512 A1* | 2/2009 | Pyun et al. ............. | 428/336 |
| 2010/0166976 A1* | 7/2010 | Lin et al. ................ | 427/512 |
| 2011/0040031 A1 | 2/2011 | Langerbeins et al. | |

FOREIGN PATENT DOCUMENTS

| | | |
|---|---|---|
| JP | 2011517718 | 6/2011 |
| WO | 03/073444 | 9/2003 |
| WO | 2005/034205 | 4/2005 |
| WO | 2007/106771 | 9/2007 |
| WO | 2007/136413 | 11/2007 |
| WO | 2009/029053 | 3/2009 |
| WO | WO2009127433 | 10/2009 |

OTHER PUBLICATIONS

Huang et al. Polymeric Materials: Science & Engineering, 2009, 101, p. 891-893.*
Australian Patent Office; International Search Report and Written Opinion in corresponding PCT application (PCT/KR2010/009126): mailed Feb. 25, 2011.
Yan-Jyi Huang, et al "Effects of Micron and Nano-Scale Inorganic/Organic Core-Shell Particle on the Volume Shrinkage in the Cure of Unsaturated Polyester and Vinyl Ester Resins" Polymeric Materials: Science & Engineering (2009) vol. 101, pp. 891-893.
Huang et al., "Effects of Micron and Nano-Scale Inorganic/Organic Core-Shell Particle on the Volume Shrinkage in the Cure of Unsaturated Polyester and Vinyl Ester Resins", Polymeric Materials: Science and Engineering (2009), vol. 101, pp. 137-139.

* cited by examiner

*Primary Examiner* — James J Seidleck
*Assistant Examiner* — S. Camilla Pourbohloul
(74) *Attorney, Agent, or Firm* — Workman Nydegger

(57) ABSTRACT

Nanoparticles can include a core linked to a polymerizable moiety that can be polymerized, cross-linked or cured. The polymerizable nanoparticles can be included in a composition for a polymerization, cross-linking or curing reaction in an amount and disposition sufficient for inhibiting or preventing volume shrinkage during polymerization, cross-linking or curing reaction. Also, the nanoparticles can be included with monomers, dendrimers, oligomers or polymers in the compositions that can be reacted to form a polymerized, cross-linked or cured product.

17 Claims, 1 Drawing Sheet

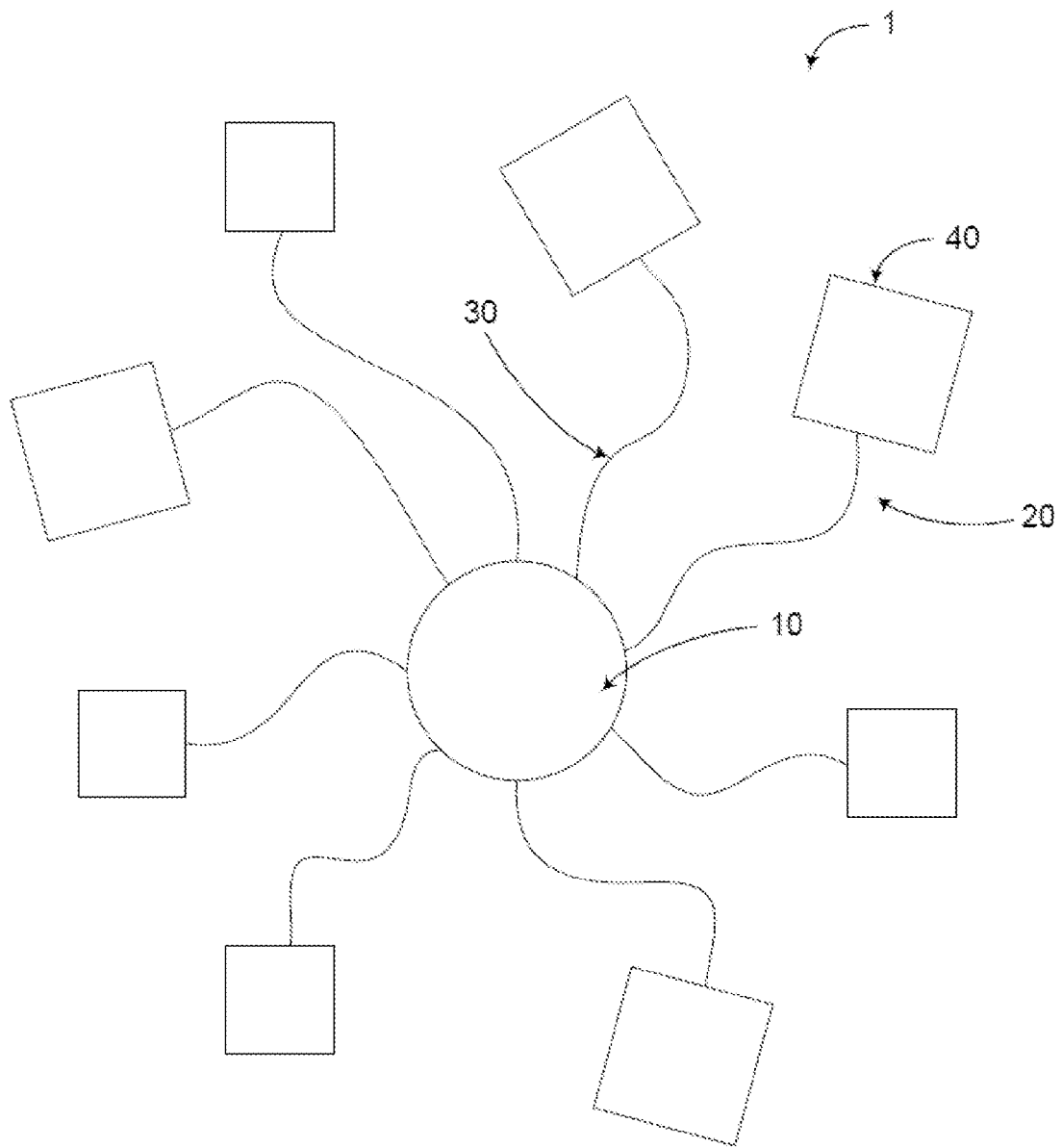

NANOPARTICLES

TECHNICAL FIELD

The described technology relates to nanoparticles.

BACKGROUND

Generally, polymerization occurs through reacting monomer molecules together in a chemical reaction to form polymer chains. In chemical compounds, polymerization reactions occur via a variety of reaction mechanisms that vary in complexity due to the functional groups present in the reacting compounds and their inherent steric effects.

The reactant monomer composition usually has a first volume prior to the polymerization process and a second, smaller volume after the polymerization. Although not intending to be limited by a particular mechanism, this may result at least in part because a void volume may exist between the individual monomers, and that void volume may be reduced when the monomers become linked together. Similarly, when a reactant composition includes dendrimers, oligomers, and/or polymers that are polymerizable or cross-linkable, the volume of polymerized or cross-linked polymers tends to be smaller than the volume of the reactant composition.

Such a reduction in volume during polymerization and/or cross-linking can impart imperfections into various manufacturing processes due to dimensional instability. Many current manufacturing processes in nanotechnologies, microelectronics, display devices and the like rely on precision, especially with regard to the placement and spacing between parts, with dimensional stability being important. The resultant products can have defects, inadequacies, or be viewed as having bad craftsmanship. Thus, it can be desirable to have a polymerization, curing, or cross-linking reaction that has dimensional stability from the reactant composition to the final product.

SUMMARY

In one embodiment, the nanoparticle can have a core; and one or more polymerizable moieties linked to the core, where the polymerizable moieties can be configured for undergoing a polymerization, cross-linking or curing reaction. In one embodiment, the nanoparticle may be used for preventing volume shrinkage during a polymerization, cross-linking or curing reaction. The nanoparticle can have an average diameter of 0.1 nm to 1,000 nm.

The core can include a nanoparticle, nanocluster, nanopowder, single crystal, nanocrystal, nanorods, nanofibers, nanocups, core-shell particle, or combination thereof and the like. The nanoparticle core can include one or more of polymers, lipids, liposomes, metals, alloys, metal oxides, ceramics, composites, quantum dots or combinations thereof and the like. The core can include gold, silver, aluminium, platinum, palladium, copper, cobalt, iron, nickel, manganese, gadolinium, molybdenum, silica, titania, iron oxide, cobalt oxide, CoCu, CoPt, FePt, CoSm, NiFe or NiFeCo, or combinations thereof and the like. The core can include gold, silver, aluminium, silica, or titania, or combinations thereof and the like.

In one embodiment, one or more of the polymerizable moieties can be reactive moieties linked to the core, or include the reactive moieties linked to the core through a linker that is associated with the core. The linker can be associated with the core by ionic, covalent, hydrophilic, hydrophobic association or any other type of association, coupling, or bonding. The linker can be a straight or branched, substituted or unsubstituted alkylene oxide; straight or branched, substituted or unsubstituted alkylene; substituted or unsubstituted cycloalkylene; substituted or unsubstituted arylene; branched or unbranched or cyclic substituted or unsubstituted arylalkylene; or combinations thereof and the like.

In one embodiment, one or more of the polymerizable moieties can be configured for polymerization through participating in plasma polymerization, step-growth polymerization, chain-growth polymerization, cationic addition polymerization, anionic addition polymerization, free-radical polymerization, ring-opening polymerization, radiation polymerization, chemical initiator polymerization, heat polymerization, Ziegler-Natta catalyst polymerization, peptide synthesis, nucleotide synthesis, or protein synthesis or any other reaction for preparing a polymer or a crosslinked polymer. For example, polymerizable moiety can be a radiation polymerizable moiety, radical polymerizable moiety or an ionic polymerizable moiety.

In one embodiment, the polymerizable moiety can be represented by

-L-X—Y wherein L represents an alkylene, alkenylene, alkynylene, alkylene oxide, $—(CH_2)_\lambda—O—(CH_2)_m$; X represents a single bond, $—O—$, $—O—(CH_2)_q—$, $—O—C(=O)—$, $—C(=O)—O—$, $—O\text{-T-}$ or $—O\text{-T-}C(=O)—$; Y represents $—P$ or $—CH_{(3-n)}P_n$;

wherein T represents arylene, P represents a reactive moiety, $\lambda$ and m independently represent 1 to 20, q represents 1 to 10 and n represents 1 to 3.

In one embodiment, the P represents (meth)acryloyl group, a vinyl group, a styryl group, cyclic ether group, a vinyl ether group, a hydroxyalkyl group, a polyoxyalkylene group or combinations thereof and the like.

In one embodiment, the nanoparticle can have 1 to 1,000 polymerizable moieties or more if possible.

In one embodiment, a method of making the nanoparticle can include: providing the core; and linking the one or more polymerizable moieties to the core, said polymerizable moieties being configured for undergoing a polymerization, cross-linking or curing reaction.

This disclosure may also relate to a composition for polymerization, cross-linking or curing reaction, which includes monomers, dendrimers, oligomers or polymers that are capable of participating in the polymerization, cross-linking or curing reaction; and the nanoparticle as described above, of which the polymerizable moieties are selected so as to be capable of reacting with the polymerizable, crosslinkable or curable functional group of the monomers, dendrimers, oligomers or polymers. The polymerizable moiety can include the same as or different chemical structure from the functional groups in the monomers, dendrimers, oligomers or polymers. For example, the nanoparticle can be comprised in an amount of 50 parts by weight or less, relative to the total weight of the monomers, dendrimers, oligomers or polymers.

This disclosure may also relate to a product that includes a polymerized, crosslinked or cured material of the composition as described above. The product can be an adhesive, a pressure-sensitive adhesive, a hard coating or a sealant, dental composition, hard plastic, foam, memory foam, elastomer, or plastomer and the like.

This disclosure may also relate to a method for polymerizing, cross-linking or curing the composition as described above: providing the composition having an initial volume; and reacting the monomers, dendrimers, oligomers or polymers with the nanoparticle to form a polymerized, crosslinked or cured product having a final volume, wherein the final volume is substantially the same as the initial volume. Accordingly, the final volume can be substantially the same as the initial volume, which can be a change of less than 10%, less than 5%, less than 1% or less than 0.5% by volume.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 shows a schematic of an illustrative embodiment of a nanoparticle comprising polymerizable moieties.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Embodiments described herein are directed to a nanoparticle that includes a core, and one or more polymerizable moieties linked to the core. The polymerizable moieties can be configured for undergoing a polymerization, cross-linking or curing reaction. In one embodiment, the polymerizable moieties may be reactive moieties linked to the core, or include the reactive moieties linked to the core through a linker that is associated with the core. In one embodiment, the reactive moiety can be any functional group, monomeric moiety, oligomeric moiety, polymeric moiety, or the like for polymerization, cross-linking or curing reaction, which is linked to the core in a manner in which it retains the ability to undergo a polymerization, cross-linking or curing reaction. While dendrimers, oligomers and polymers can be involved in further polymerization, cross-linking or curing reaction, such entities can be considered to be reactive moieties as described herein for the purposes of further polymerization, cross-linking or curing reaction where these entities are linked to a nanoparticle. Also, in this disclosure, the polymerizable moiety may be considered as including the polymerizable, cross-linkable and curable moiety. Also, in this disclosure, the polymerization may be considered as including the polymerization, cross-linking and curing reaction.

In some embodiment, the nanoparticles may be used for preventing volume shrinkage during a polymerization reaction. Accordingly, embodiments described herein may be directed to a use of the nanoparticle for preventing volume shrinkage during a polymerization reaction.

In some embodiments, one or more of the polymerizable moieties can include the reactive moieties linked to the nanoparticle core through a linker that can be associated with the core through ionic, covalent, hydrophilic, hydrophobic association or any other type of association, coupling, bonding, or the like. The linker can include, but is not limited to, a straight or branched, substituted or unsubstituted alkylene oxide, straight or branched, substituted or unsubstituted alkylene, substituted or unsubstituted cycloalkylene, substituted or unsubstituted arylene, branched or unbranched or cyclic, substituted or unsubstituted arylalkylene, or combinations thereof and the like.

In one embodiment, the nanoparticle can be included in a composition for polymerization reaction with a monomer, a dendrimer, an oligomer or a polymer such that the nanoparticle reacts with the monomer, dendrimer, oligomer or polymer to form a polymerized, a cross-linked or cured product. The nanoparticle can include a reactive moiety that is the same as or is compatible chemical structure with the monomer, dendrimer, oligomer or polymer. Also, the composition can be prepared to include a sufficient amount of the nanoparticle in order to have a first volume prior to polymerizing, cross-linking or curing reaction, and after polymerizing, cross-linking or curing reaction can provide the polymerized, cross-linked or cured product that has substantially the same volume as the first volume. As such, the polymerization can be considered to be constant volume polymerization because the process inhibits or prevents volume shrinkage. For example, the polymerized, cross-linked or cured volume can be substantially the same as the initial volume, which can be a change of less than 10%, less than 5%, less than 1% or less than 0.5% by volume. Thus, the polymerized, cross-linked or cured product, such as an adhesive, a pressure-sensitive adhesive, a hard coating or a sealant, dental composition, hard plastic, foam, memory foam, elastomer, or plastomer and the like, can have substantially the same volume as the composition before the polymerization reaction.

The process of constant volume polymerization can provide dimensional stability during manufacturing processes. For example, microelectronic devices or display devices can utilize photo-curable sealant and/or adhesives between parts or components. Without constant volume polymerization, after curing such photo-curable sealant by light illumination, the volume of the product can be reduced from the initial volume so as to make the adhesion or dimensional stability poor and unfavorable, especially considering devices where exact placement of components is important or desirable. Thus, the process of constant volume polymerization can avoid shrinkage by the presence of the nanoparticle in the composition for polymerization, cross-linking or curing reaction.

Such a polymerizable nanoparticle can include any nanoparticle that can be linked to a polymerizable moiety, such as vinyl, epoxy, oxetane, or other polymerizable groups. The polymerizable nanoparticle can be mixed with a compatible monomer, dendrimer, oligomer or polymer that can react with the reactive moiety of the nanoparticle. The reactive groups in the monomer can begin to polymerize, and the macro-end reactive species can undergo propagation through the reactive moiety on the surface of nanoparticles. Any free volume quenching behavior can be lessened because of the constant volume of the nanoparticle and the volume arrangement of the polymer with respect to the nanoparticle.

The nanoparticle can be any particle which has an average diameter ranging from approximately 0.1 nm to approximately 1,000 nm. In one embodiment, the nanoparticle may have an average diameter ranging from approximately 1 nm to approximately 950 nm, approximately 1 nm to approximately 900 nm, approximately 1 nm to approximately 850 nm, approximately 1 nm to approximately 800 nm, approximately 1 nm to approximately 750 nm, approximately 1 nm to approximately 700 nm, approximately 1 nm to approximately 650 nm, approximately 1 nm to approximately 600 nm, approximately 1 nm to approximately 550 nm, approximately 1 nm to approximately 500 nm, approximately 1 nm to approximately 450 nm, approximately 1 nm to approximately 400 nm, approximately 1 nm to approximately 350 nm, approximately 1 nm to approximately 300 nm, approximately 1 nm to approximately 250 nm, approximately 1 nm to approximately 200 nm, approximately 1 nm to approximately 150 nm, approximately 1 nm to approximately 100 nm, approximately 1 nm to approximately 90 nm, approximately 1 nm to approximately 70 nm, approximately 1 nm to approximately 50 nm, approximately 1 nm to approximately 30 nm, approximately 1 nm to approximately 20 nm, approximately 1 nm to approximately 10 nm or approximately 1 nm to approximately 5 nm. In another embodiment, the nanoparticle may have an average diameter of approximately 0.1 nm, approximately 0.5 nm, approximately 1 nm, approximately 2 nm, approximately 3 nm, approximately 5 nm, approximately 10 nm, approximately 20 nm, approximately 30 nm, approximately 40 nm, approximately 50 nm, approximately 60 nm, approximately 70 nm, approximately 80 nm, approximately 90 nm, approximately 100 nm, approximately 200 nm, approximately 300 nm, approximately 400 nm, approximately 500 nm, approximately 600 nm, approximately 700 nm, approximately 800 nm, approximately 900 nm or approximately 1,000 nm.

FIG. 1 shows a schematic of an illustrative embodiment of the nanoparticle. Referring to FIG. 1, the nanoparticle 1 includes a core 10 and a polymerizable moiety 20. In one embodiment, the polymerizable moiety 20 may include the reactive moiety 40 that participates in the polymerization, cross-linking or curing reaction. In one embodiment, the polymerizable moiety 20 may include a reactive moiety 40 and a linker 30 that is linked to the core 10.

The core 10 can be formed from a variety of nanomaterials and in a variety of shapes, hardness or other characteristics. The core can be in a form of a nanoparticle, nanocluster, nanopowder, single crystal, nanocrystal, nanorods, nanofibers, nanocups, core-shell particle, or the like. The nanoparticle can be rigid, malleable, spherical, polyhedral, amorphous, or the like. The nanomaterials can be selected from polymers, lipids, liposomes, metals, alloys, metal oxides, ceramics, composites, quantum dots, or the like.

Examples of materials can include a metal, an oxide or an alloy material. The metal can be an alkali metal, alkaline earth metal, transition metal, post-transition metal, lanthanoids, actinoids, or the like.

The alkali metals: Lithium, Sodium, Potassium, Rubidium, Caesium, and Francium. The alkaline earth metals: Beryllium, Magnesium, Calcium, Strontium, Barium, and Radium. The transition metals: Zinc, Molybdenum, Cadmium, Scandium, Titanium, Vanadium, Chromium, Manganese, Iron, Cobalt, Nickel, Copper, Yttrium, Zirconium, Niobium, Technetium, Ruthenium, Rhodium, Palladium, Silver, Hafnium, Tantalum, Tungsten, Rhenium, Osmium, Iridium, Platinum, Gold, Mercury, Rutherfordium, Dubnium, Seaborgium, Bohrium, Hassium, Meitnerium, Darmstadtium, Roentgenium, and ununbium. The post-transition metals: Aluminium, Gallium, Indium, Tin, Thallium, Lead, Bismuth, Ununtrium, Ununquadium, Ununpentium, and Ununhexium. The lanthanoids: Lanthanum, Cerium, Praseodymium, Neodymium, Promethium, Samarium, Europium, Gadolinium, Terbium, Dysprosium, Holmium, Erbium, Thulium, Ytterbium, and Lutetium. The actinoids: Actinium, Thorium, Protactinium, Uranium, Neptunium, Plutonium, Americium, Curium, Berkelium, Californium, Einsteinium, Fermium, Mendelevium, Nobelium, and Lawrencium. Some of these elements may be more favorable for some applications. Other elements, such as radioactive elements may be useful in nanoparticles for producing radioactive polymers.

Alloys can be prepared from any combination, amount, or ratio of the metals. Examples can include: CoCu, CoPt, FePt, CoSm, NiFe, NiFeCo or the like.

The oxides can be prepared from appropriate metals. Examples can include silica, titania, iron oxide, cobalt oxide, and the like.

In one embodiment, the core may include gold, silver, aluminium, platinum, palladium, copper, cobalt, iron, nickel, manganese, gadolinium, molybdenum, silica, titania, iron oxide, cobalt oxide, CoCu, CoPt, FePt, CoSm, NiFe or NiFeCo, or combinations thereof and the like. In another embodiment, the core may include gold, silver, aluminium, silica, or titania, or combinations thereof and the like.

Methods for preparing the core are not limited, and any conventional method used in the field can be applied. In one embodiment, the core may be prepared through an attrition method. In the attrition method, macro or micro scale particles are ground in various attrition means, such as a ball mill, a planetary ball mill or other size reducing mechanism. In another embodiment, the core may be prepared through a pyrolysis method, in which a vaporous precursor (liquid or gas) is forced through an orifice at high pressure and burned. The resulting solid (a version of soot) is air classified to recover oxide particles from by-product gases. In still another embodiment, the core may be prepared by using thermal plasma. The thermal plasma may deliver the energy necessary to cause evaporation of small micrometer size particles. The thermal plasma temperatures are in the order of approximately 10,000 K, so that solid powder easily evaporates. The core may be formed upon cooling while exiting the plasma region. In still another embodiment, the core may be prepared through inert-gas condensation, in which metals are vaporized in a vacuum chamber and then super cooled with an inert gas stream; the supercooled metal vapor condenses into nanometer-sized particles. In still another embodiment, the core may be prepared through a wet-chemical technique, such as a sol-gel method. In a sol-gel process, a chemical solution (sol) is used as a starting material, and the solution may act as the precursor for an integrated network (gel) of discrete nanoparticles.

One skilled in the art will appreciate that, for this and other processes and methods stated herein, the functions performed in the process and methods may be implemented in differing order. Furthermore, the outlined steps and operations are only provided as examples, and some of the steps and operations may be optional, combined into fewer steps and operations, or expanded into additional steps and operations without detracting from the essence of the stated embodiments.

The core 10 can be associated with the polymerizable moiety 20 by a variety of interactions, bonding, or couplings. For example, the core and polymerizable moiety may be associated by ionic interaction, hydrogen bonding, hydrophobic interaction, hydrophilic interaction, covalent binding, or any other means of chemical association.

The polymerizable moiety 20 can include a linker 30 that can provide for the association with the core 10. The linker 30 can be any of a variety of different types that have the capacity to associate with the core 10 and extend the reactive moiety 40 away from the core 10. The linkers can be hydrocarbon (e.g., alkyl), polymeric, polypeptide, polynucleotide, or the like. The polymer linkers can include star polymers, comb polymers, brush polymers, ladders, and dendrimers. The linkers can be uniform, continuous, linear, branched, or segmented so that each segments has an individual characteristic and/or functionality in spacing the reactive moiety from the core. Segmented linkers can be configured to self-form various three-dimensional conformations similar to protein folding, lipid association, and the like. For example, the individual segments can be ionic, cationic anionic, hydrophilic, hydrophobic, or other property and combinations thereof.

The reactive moiety can include any type of functional group or monomeric moiety that is capable of participating in a polymerizing, cross-linking or curing reaction. The functional group or monomeric moiety may be capable of participating in plasma polymerization, step-growth polymerization, chain-growth polymerization, cationic addition polymerization, anionic addition polymerization, free-radical polymerization, ring-opening polymerization, radiation polymerization, chemical initiator polymerization, heat polymerization, Ziegler-Natta catalyst polymerization, peptide synthesis, nucleotide synthesis, protein synthesis, or other. The functional group or monomeric moiety may participate in polymerization with or without a catalyst. For example the functional group or monomeric moiety can include alkenes, carbonyls, formaldehydes, formaldehyde hydrates, or the like.

In another embodiment, the polymerizable moiety 20 may be a radiation polymerizable moiety. The term "radiation" as used herein includes, but is not limited to, electromagnetic radiation such as microwaves, infrared radiation, ultraviolet (UV) radiation, X-rays and γ-rays; as well as particle beams such as α-particle beams, proton beams, neutron beams and electron beams.

In still another embodiment, the polymerizable moiety may be a radical polymerizable moiety or an ionic polymerizable moiety. A radical polymerizable moiety may be a (meth)acryloyl group, a vinyl group, a styryl group, and the like. A radical polymerizable moiety may be a vinyl group or (meth)acryloyl group. The term "(meth)acryloyl group" as used herein refers to an acryloyl group and a methacryloyl group.

In one embodiment, the polymerizable moiety may be a cyclic ether group, a vinyl ether group, a hydroxyalkyl group, a polyoxyalkylene group, and the like. The term "cyclic ether" as used herein includes, but is not limited to, an epoxy moiety, an alicyclic epoxy moiety and an oxetane moiety. The term "alicyclic epoxy moiety" as used herein includes, but is not limited to, an epoxycycloalkyl group, such as a 3,4-epoxycyclopentyl group or a 3,4-epoxycyclohexyl group. In another embodiment, the ionic polymerizable moiety may be a cyclic ether group or a vinyl ether group.

In the above polymerizable moiety, the alkyl may be an alkyl having 1 to 20 carbon atom(s), 1 to 16 carbon atom(s), 1 to 12 carbon atom(s), 1 to 8 carbon atom(s) or 1 to 4 carbon atom(s). In another embodiment, the alkyl may be methyl, ethyl, propyl, butyl, pentyl or hexyl. In one embodiment, the alkyl may have a linear or branched, or cyclic or acyclic structure.

In the above polymerizable moiety, the alkylene may be an alkylene having 1 to 20 carbon atom(s), 1 to 16 carbon atom(s), 1 to 12 carbon atom(s), 1 to 8 carbon atom(s) or 1 to 4 carbon atom(s). In another embodiment, the alkylene may be methylene, ethylene, propylene, butylene, pentylene or hexylene. In one embodiment, the alkylene may have a linear or branched, or cyclic or acyclic structure.

In one embodiment, the polymerizable moiety may be represented by formula 1 below:

-L-X—Y     [formula 1]

wherein L represents an alkylene, alkenylene, alkynylene, alkylene oxide, —$(CH_2)_\lambda$—O—$(CH_2)_m$—; X represents a single bond, —O—, —O—$(CH_2)_q$—, —O—C(=O)—, —C(=O)—O—, —O-T- or —O-T-C(=O)—; and Y represents —P or —$CH_{(3-n)}P_n$, where T represents arylene, P represents a reactive moiety, λ and m independently represent 1 to 20, 1 to 15, 1 to 10 or 1 to 5, or even 1, 2, 3, 4, or 5; q represents 1 to 10 or 1 to 5, or even 1, 2, 3, 4, or 5; and n represents 1, 2, or 3.

The term "single bond" used herein refers to the case in which there are no elements between "L" and "Y", that is, "L" and "Y" are directly bonded.

The term "arylene" used herein refers to a bivalent group derived from an aromatic hydrocarbon. In one embodiment, the aromatic hydrocarbon may have 6 to 22 ring-membered atoms, 6 to 18 ring-membered atoms, 6 to 14 ring-membered atoms or 6 to 10 ring-membered atoms. In another embodiment, the aromatic hydrocarbon may be benzene, naphthalene, anthracene, and the like. Multi-ring arylenes can include more than 22 ring atoms. The arylene can be substituted or unsubstituted.

In formula 1 above, the alkylene, alkenylene, alkynylene or alkylene oxide can include any carbon chain having 1 to 20 carbon atom(s), 1 to 16 carbon atom(s), 1 to 12 carbon atom(s), 1 to 8 carbon atom(s) or 1 to 4 carbon atom(s). For example, the alkylene may be methylene, ethylene, propylene, butylene or pentylene. The alkylene, alkenylene, alkynylene or alkylene oxide may have a linear or branched, or cyclic or acyclic structure. The alkylene, alkenylene, alkynylene or alkylene oxide can be substituted or unsubstituted.

In formula 1 above, the alkylene oxide may be represented by -$(A-O)_p$— or —$(O-A)_p$-, in which A represents alkylene and p is in the range of 1 to 10, 1 to 8, 1 to 6, 1 to 4 or 1 to 2.

In formula 1 above, X may be a single bond, —O—, —O—$(CH_2)_q$—, —O—C(=O)—, —O-T- or —O-T-C(=O)—, in which T represents phenylene or naphthylene, and q represents 1 to 4.

In formula 1 above, P can be a reactive moiety such as a radiation polymerizable moiety, radical polymerizable moiety, ionic polymerizable moiety, or the like. For example, the reactive moiety may include a (meth)acryloyl group, a vinyl group, a styryl group, cyclic ether group, vinyl ether group, a hydroxyalkyl group, or a polyoxyalkylene group. In still another embodiment, P may be a (meth)acryloyl group, a vinyl group, a styryl group, an epoxy group, an oxetane group or a vinyl ether group.

In one embodiment, the polymerizable moiety may be substituted by at least one substituent, such as "n" substituents. The substituent may be hydrogen, a halogen or an alkyl, or an aryl group.

In one embodiment, the nanoparticle may have as many polymerizable moieties as possible or any number less as desired as long as 1 polymerizable moiety is present. For example, the nanoparticle may include 1 to 1,000, 1 to 900, 1 to 800, 1 to 700, 1 to 600, 1 to 500, 1 to 400, 1 to 300, 1 to 200 or 1 to 100 polymerizable moieties. In another embodiment, the nanoparticle may include 4 to 70, 4 to 50, 4 to 30, 4 to 20 or 4 to 10 polymerizable moieties. In still another embodiment, the nanoparticle may include 16 to 70, 16 to 50, 16 to 30 or 16 to 20 polymerizable moieties. In still another embodiment, the nanoparticle may include 4, 7, 10, 13, 16, 19, 21 or 24 polymerizable moieties.

Methods for preparing the nanoparticle are not particularly limited. In one embodiment, the nanoparticle may be prepared by providing the core; and linking the one or more polymerizable moieties to the core. In one embodiment, the polymerizable moieties may be linked to the core by contacting the core and a compound represented by formula 2 below in an appropriate medium.

Q-L-X—Y        [formula 2]

wherein Q represents a moiety capable of forming a bond or an interaction to the surface of the core, and L, X and Y are the same as described in formula 1.

In formula 2 above, the kind of moiety capable of forming a bond or an interaction to the surface of the core is not particularly limited, and can be selected considering the kind of core. For example, the moiety may be, but not limited to, thiol (HS), carboxy (COOH), hydroxy (OH), cyano (CN), a halogen, an alkyl substituted with a halogen, and the like. When the core is a metal or alloy material, such as gold (Au), silver (Ag), copper (Cu) or palladium (Pd), Q may be a thiol (SH) or cyano group (CN). Also, when the core is oxide, such as silica or titania, Q may be hydroxy (OH), carboxy (COOH) or a halogen such as bromine (Br).

The kind of medium in which the core and the compound represented by formula 2 are contacted is not limited, and can include any solvent sufficient for maintaining the reaction. The medium may be ethers such as butyl ether, hexyl ether, octyl ether or decyl ether; heterocycles such as pyridine or tetrahydrofuran; an aromatic compound such as toluene, xylene, mesitylene or benzene; sulfoxides such dimethyl sulfoxide; amides such as dimethylformamide; alcohols such as octyl alcohol or decanol; hydrocarbons such as pentane, hexane, heptane, octane, decane, dodecane, tetradecane or hexadecane; or aqueous mediums such as water.

In one embodiment, the contact between the core and the compound represented by formula 2 may be progressed under a temperature of approximately 10° C. to 200° C., or approximately 25° C. to 150° C.

In one embodiment, the contact between the core and the compound represented by formula 2 may be progressed for approximately 1 hour to 40 hours, or approximately 6 hours to 24 hours.

One skilled in the art will appreciate that, for this and other processes and methods stated herein, the functions performed in the process and methods may be implemented in differing order. Furthermore, the outlined steps and operations are only provided as examples, and some of the steps and operations may be optional, combined into fewer steps and operations, or expanded into additional steps and operations without detracting from the essence of the stated embodiments.

In one embodiment, the nanoparticle can be combined in a reactive composition with a monomer, a dendrimer, an oligomer or a polymer for polymerization, cross-linking or curing reaction. The monomer, dendrimer, oligomer or polymer may have an identical structure or functional group as the polymerizable moiety in the polymerizable nanoparticle, or it may have a different but compatible structure or functional group. Also, a kit can include the nanoparticle and monomer separately from each other in a mixable format. The kit can also include a polymerization catalyst, facilitator, or accelerated separately or with either nanoparticle or the monomer.

For example, the polymerizable monomer can include methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, and copolymerizable acrylated oligomers, phosphoric acid derivatives, carboxylic acid derivatives of ethylenically unsaturated monomers, vinyl compounds, styrene, diallyl phthalate, divinyl succinate, divinyl adipate, divinylphthalate or other monomers. Additionally, mixtures of two or more of these polymerizable monomers can be used if desired. However, it should be recognized that this is not an exhaustive listing of polymerizable monomers, and other polymerizable monomers can be used in accordance with the present disclosure.

In one embodiment, a nanoparticle can be included in a composition with a monomer, dendrimer, oligomer or polymer that is sufficient for conducting a polymerization reaction. The composition can be maintained in a condition and with any other polymerization reagents such that polymerization occurs between the nanoparticles and monomers, dendrimers, oligomers or polymers within the composition. The reaction is conducted such that the amount or ratio of the nanoparticle; monomer, dendrimer, oligomer or polymer; and any other reagent or solvent has an initial volume V1 and a final volume V2. V1 and V2 can be identical such that volume does not change during the reaction. Also, the change between V1 and V2 can be negligible or a sufficiently small amount such that the polymerization reaction can be utilized for an application where the final polymer can function as desired and can be considered to be within a reasonable standard deviation. For example, in some instances, it can be desirable for the change from V1 to V2 to be less than 10%, less than 5%, less than 1% or, less that 0.1%. Thus, the nanoparticle can be used for inhibiting or preventing volume shrinkage during a polymerization process.

When the polymerization process progresses in the presence of the nanoparticle as described above, reactions may occur both between the functional groups in monomers, dendrimers, oligomers or polymers and between the functional group in the monomer, dendrimers, oligomers or polymers and the polymerizable moiety in the nanoparticle, and thereby volume shrinkage may be inhibited or prevented.

The polymerizable moiety contained in the nanoparticle may be selected so as to be capable of reacting with polymerizable, cross-linkable or curable functional groups of the monomers, dendrimers, oligomers or polymers. In one embodiment, the polymerizable moiety of the nanoparticle may have an identical chemical structure with the functional group of the monomers, dendrimers, oligomers or polymers.

In the above composition, the kinds of monomers, dendrimers, oligomers or polymers are not particularly limited, and can be selected considering the polymerization process. The monomers, dendrimers, oligomers or polymers can be selected to be sufficient for reacting with the nanoparticle, such as in a radiation polymerization process, a radical polymerization process, or other polymerization process.

In one embodiment, the radical polymerization process may be initiated by certain compounds capable of being broken down into two radicals at a temperature just above room temperature, such as organic peroxides or azo compounds; photosensitive molecules, which under influence of light, get into an excited state or react with other molecules forming radicals; or a redox-system with transfer of one electron during the reaction.

Typically, free radical polymerization requires an initiator to generate a free radical. Various types of initiators can produce a free radical upon being exposed to light, heat, or chemicals. The initiator compounds are provided into the compositions in an effective amount to initiate or enhance the rate of polymerization or cross-linking.

Photo-initiators are a group of compounds that will generate a free radical when exposed to light having a specific wavelength. As such, different photo-initiators can be selected depending on the wavelength of light that will initiate the polymerization. Examples of photo-initiators can include benzophenone, benzoin, 9,10-phenanthrenequinone, diacetyl, furil, anisil, 4,4'-dichlorobenzil, 4,4'-dialkoxybenzil, phenylpropanedione, acylphosphine oxides, camphorquinone, derivatives thereof, and the like. Photopolymerization can be initiated, for example, by irradiation with light having a wavelength of from about 400 nm to about 500 nm.

Heat-initiators can be used in hot-curing systems. Some heat-initiators can be activated with temperatures less than 150° C. Examples of heat-initiators can include t-butyl peroxide, dibenzoyl peroxide, dilauroyl peroxide, t-butyl peroctoate, t-butyl perbenzoate, and the like.

On the other hand, in certain applications a chemical-initiator, which typically is a system of at least two co-initiators that generate a free radical, can be used to induce polymerization. These chemical-initiator systems use a reactive pair, for example, benzoyl peroxide, lauryol peroxide, or dibenzoyl peroxide, in combination with a N,N-dimethyl-p-toluidine, N,N-dihydroxyethyl-p-toluidine, and other similar amines. Alternatively, a combined system including a photo-initiator, heat-initiator, and/or chemical-initiator can be used.

The concentration of the initiator may depend on the concentration of the nanoparticle, and the monomer, dendrimer, oligomer or polymer. Additionally, the concentration of the initiator may depend on the type of initiator. For example, the reactive composition can include a initiator at a range of from about 0.001% to about 5% by weight, a range of from about 0.01% to about 2.5% by weight, or a range of from about 0.1% to about 1% by weight. However, the concentration of initiator can be varied depending on the type of initiator and/or type of resin as well as the desired properties of the composition and final product.

In another embodiment, the monomers may be ones used in an ionic polymerization process, such as a cationic polymerization process. In the ionic polymerization process, the growth of a polymer chain may proceed by reaction(s) between monomer(s) and reactive site(s) on the polymer chain with regeneration of the reactive site(s) at the end of each growth step.

In the above composition, the amount of nanoparticles is not particularly limited, and may be determined considering the kind of the reactions, the desired product, and the like. The amount or ratio of the nanoparticle that is sufficient for inhibition or prevention of volume shrinkage for a particular polymerization can be determined using standard tests described herein and/or known in the art. The reaction composition can include less than 50%, less than 25%, less than 10%, or less than 5% or less than 1% by weight or by volume of the reaction composition. For example, the nanoparticle may be included in an amount of approximately 20 parts by weight or less, approximately 15 parts by weight or less, approximately 10 parts by weight or less, approximately 5 parts by weight or less, or approximately 3 to 5 parts by weight, relative to the total weight of the monomers, or approximately 3 parts by weight or approximately 2 parts by weight, relative to the total weight of the monomers, dendrimers, oligomers or polymers, or of the total reaction composition.

In some instances, it can be beneficial to have a high amount, such over 50%, and possibly over 75%; however, this may cause swelling and an increase in volume. In some instances, it may be advantageous to cause an increase in volume, and therefore the nanoparticles can be used in amounts to cause swelling or volume expansion for increases of 1%, up to 10%, up to 25%, or 50%. It is even possible to conduct the reaction in about 100% nanoparticles for swelling.

In one embodiment, the composition for polymerization, cross-linking or curing reaction may further include conventional additives usable in each reaction, such as an initiator, a chain transfer agent, an inhibitor, a stabilizer, a cross-linking agent, a curing agent and the like.

In one embodiment, a product including the polymerized material of the composition can be obtained by conducting the polymerization reaction with the nanoparticle and monomers, dendrimers, oligomers or polymers. The product can be any hard, rigid structure, or bendable, flexible structure commonly associated with polymers, plastics, adhesives, and the like.

In one embodiment, the product may be an adhesive, a pressure-sensitive adhesive, a hard coating, a sealant, dental composition, hard plastic, foam, memory foam, elastomer, plastomer, or the like.

Additionally, the nanoparticle can include a reactive moiety that is configured to undergo a cross-linking or curing reaction. As such, cross-linking or curing can be performed with the nanoparticle in a similar manner as polymerization so as to inhibit or prevent cross-linking or curing volume shrinkage. For example, in some instances, the nanoparticle having the reactive group can be cross-linked with itself. In another example, the nanoparticle can be cross-linked with other substances, such as polymers. A cross-linking reaction can include the nanoparticle having the reactive group as well as a cross-linking reagent.

DEFINITIONS

The term "radical polymerization process" as used herein refers to a type of polymerization reaction in which the reactive center of a polymer chain consists of a radical.

The term "ionic polymerization process" as used herein refers to a type of chain polymerization reaction in which the kinetic-chain carriers are ions or ion pairs.

As used herein, the term "alkyl" or "aliphatic" can refer to a hydrocarbyl moiety, such as an hydrocarbon group, that can be straight or branched, saturated or unsaturated, and/or substituted or unsubstituted, which has twenty or less carbons in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an alkyl or aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also include modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, tetrahydrofuran, and pyrrolidino.

"Alkylene" refers to a linear or branched saturated divalent hydrocarbon radical. Examples of the alkylene group include, without limitation, methylene, ethylene, propylene, butylenes, and the like.

"Heteroalkylene" refers to an alkylene chain as described above, in which one or more C-atoms have in each case been replaced by a heteroatom mutually independently selected from the group comprising oxygen, sulfur and nitrogen (NH). Heteroalkylene groups can have 1, 2 or 3 heteroatom(s), particularly one heteroatom, selected from the group comprising oxygen, sulfur and nitrogen (NH) as the chain member(s). Heteroalkylene groups can be 2- to 20 membered or 2- to 12-membered, particularly 2- to 6-membered, and more particularly 2- or 3-membered. Any alkylene can be a heteroalkylene.

Alkyleneoxy" refers to a divalent group represented by the formula -(alkylene)-O— and includes, for example, a methyleneoxy, an ethyleneoxy, a propyleneoxy, a dimethylenedioxy, and the like. The linker group can include an alkyleneoxy.

"Alkylenedioxy" refers to a divalent group represented by the formula —O-(alkylene)-O— and includes, for example, a methylenedioxy, an ethylenedioxy, a propylenedioxy, a dimethylenedioxy, and the like. The linker group can include an alkylenedioxy.

As used herein, the term "aryl" or "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present include benzene, benzyl, toluene, xylene, and the like. The aromatic compound can include hetero atoms so as to be a hetero aromatic such as pyridine, furan, and the like. Also, an aromatic can be a polycyclic aromatic such as naphthalene, anthracene, phenanthrene, polycyclic aromatic hydrocarbons, indole, quinoline, isoquinoline, and the like. Any aryl herein can be a heteroaryl or polyaryl.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$, where R can be any R group described herein. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "halo" means fluoro, chloro, bromo, or iodo.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins, and any of which can be used as linkers.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. The amino acids can be natural, unnatural, common, essential, non-essential or analogs or derivatives thereof. The linkers can include amino acids or polypeptides.

As used herein, the term "nucleotide" is meant to refer to a ribonucleotide, a deoxyribonucleotide, or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotides are well known in the art. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, substitution of 5-bromo-uracil, and 2'-position sugar modifications (e.g., 2' modifications). Such modifications include sugar-modified ribonucleotides in which the 2'-OH is replaced by a group such as an H, OR, R, halo, SH, SR, $NH_2$, NHR, $NR_2$, or CN, wherein R is an alkyl or aliphatic moiety. Nucleotide analogs are also meant to include nucleotides with bases such as inosine, queuosine, xanthine, sugars such as 2'-methyl ribose, non-natural phosphodiester linkages such as methylphosphonates, phosphorothioates, and peptides. The linker can include one or more nucleotides.

As used herein, the term "polynucleotide" is meant to refer to polymers of nucleotides linked together through internucleotide linkages. Also, a polynucleotide includes DNA, RNA, DNA/RNA, hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides. Also, polynucleotides include nucleotides with various modifications or having attachments of various entities or moieties to the nucleotide units at any position. The linkers can include polynucleotides, as either a single chain or a double stranded nucleic acid.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member of subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purpose of illustration, and that various modifications may be made without departing from the scope and spirit of the present disclosure. Accordingly, the various embodiments disclosed herein are not intended to be limiting, with the true scope and spirit being indicated by the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An isolated nanoparticle for preventing volume shrinkage during a polymerization reaction, comprising:
   a core; and
   one or more un-polymerized, polymerizable moieties linked to the core,
   said un-polymerized, polymerizable moieties of the isolated nanoparticle being configured for undergoing a polymerization reaction when the isolated nanoparticle is added to a polymerizable composition, wherein the polymerizable composition includes monomers, dendrimers, oligomers or polymers that are capable of participating in the polymerization reaction with the one or more un-polymerized, polymerizable moieties linked to the core, wherein the un-polymerized, polymerizable moieties are represented by -L-X—Y wherein L represents an alkylene, alkenylene, alkynylene, alkylene oxide, —(CH2)$_\lambda$—O—(CH2)$_m$—; X represents a single bond, —O—, —O—(CH2)$_q$—, —O—C(=O)—, —C(=O)—O—, —O—T— or —O—T—C(=O)—; Y represents —P or —CH$_{(3-n)}$P$_n$;
   where T represents arylene, P represents a reactive moiety, $\lambda$ and m independently represent 1 to 20, q represents 1 to 10 and n represents 1 to 3.

2. The isolated nanoparticle according to claim 1, having an average diameter of 0.1 nm to 1,000 nm.

3. The isolated nanoparticle according to claim 1, wherein the core includes a nanoparticle, nanocluster, nanopowder, single crystal, nanocrystal, nanorods, nanofibers, nanocups, core-shell particle, or combination thereof.

4. The isolated nanoparticle according to claim 1, wherein the core includes gold, silver, aluminium, platinum, palladium, copper, cobalt, iron, nickel, manganese, gadolinium, molybdenum, silica, titania, iron oxide, cobalt oxide, CoCu, CoPt, FePt, CoSm, NiFe, NiFeCo, or combination thereof.

5. The isolated nanoparticle according to claim 1, wherein the un-polymerized, polymerizable moieties comprise one or more reactive moieties linked to the core through a linker that is associated with the core.

6. The isolated nanoparticle according to claim 1, wherein one or more of the un-polymerized, polymerizable moieties is configured for polymerization through participating in plasma polymerization, step-growth polymerization, chain-growth polymerization, cationic addition polymerization, anionic addition polymerization, free-radical polymerization, ring-opening polymerization, radiation polymerization, chemical initiator polymerization, heat polymerization, Ziegler-Natta catalyst polymerization, peptide synthesis, nucleotide synthesis, or protein synthesis.

7. The isolated nanoparticle according to claim 1, wherein the un-polymerized, polymerizable moieties are radiation polymerizable, radical polymerizable or ionic polymerizable.

8. The isolated nanoparticle according to claim 1, wherein P represents (meth)acryloyl group, a vinyl group, a styryl group, cyclic ether group, a vinyl ether group, a hydroxyalkyl group, a polyoxyalkylene group, or combination thereof.

9. The isolated nanoparticle according to claim 1, having 1 to 1,000 un-polymerized, polymerizable moieties.

10. A method of making the nanoparticle as in claim 1, the method comprising:
    providing the core; and
    linking the one or more un-polymerized, polymerizable moieties to the core.

11. A composition for a polymerization, cross-linking or curing reaction, comprising:
    monomers, dendrimers, oligomers or polymers containing un-polymerized, polymerizable functional groups capable of participating in the polymerization reaction; and
    an isolated nanoparticle, including:
       a core; and
       one or more un-polymerized, polymerizable moieties linked to the core,
    wherein the un-polymerized, polymerizable moieties of the nanoparticle are selected so as to be capable of reacting with the un-polymerized, polymerizable functional groups of the polymerizable composition, wherein the un-polymerized, polymerizable moieties are represented by
    -L-X—Y wherein L represents an alkylene, alkenylene, alkynylene, alkylene oxide, —(CH2)$_\lambda$—O—(CH2)$_m$—; X represents a single bond, —O—, —O—(CH2)$_q$—, —O—C(=O)—, —C(=O)—O—, —O-T- or —O-T-C(=O)—; Y represents —P or —CH$_{(3-n)}$P$_n$;

where T represents arylene, P represents a reactive moiety, λ and m independently represent 1 to 20, q represents 1 to 10 and n represents 1 to 3.

12. The composition for a polymerization reaction according to claim 11, wherein the un-polymerized, polymerizable moieties include the same chemical structure as the polymerizable functional group of the monomers, dendrimers, oligomers or polymers.

13. The composition for a polymerization reaction according to claim 11, wherein the nanoparticle is comprised in an amount of 50 parts by weight or less, relative to the total weight of the monomers, dendrimers, oligomers or polymers.

14. A product comprising;
a polymerized material of the composition as in claim 11.

15. The product according to claim 14, wherein the polymerized material is an adhesive, a pressure-sensitive adhesive, a hard coating or a sealant, dental composition, hard plastic, foam, memory foam, elastomer, or plastomer.

16. A method for polymerizing a composition, comprising:
providing a composition having an initial volume, the composition including:
monomers, dendrimers, oligomers or polymers capable of participating in a polymerization reaction, cross-linking or curing reaction; and
an isolated nanoparticle, including:
a core; and
one or more un-polymerized, polymerizable moieties linked to the core,
wherein the un-polymerized, polymerizable moiety moieties of the nanoparticle are selected so as to be capable of participating in a polymerization reaction with the monomers, dendrimers, oligomers or polymers, wherein the un-polymerized, polymerizable moieties are represented by
-L-X—Y wherein L represents an alkylene, alkenylene, alkynylene, alkylene oxide, —(CH2)$_λ$—O—(CH2)$_m$—; X represents a single bond, —O—, —O—(CH2)$_q$—, —O—C(=O)—, —C(=O)—O—, —O-T- or —O-T-C(=O)—; Y represents —P or —CH$_{(3-n)}$P$_n$;
where T represents arylene, P represents a reactive moiety, λ and m independently represent 1 to 20, q represents 1 to 10 and n represents 1 to 3; and
reacting the monomer, dendrimer, oligomer or polymer with the nanoparticle to form a polymerized material having a final volume,
wherein the final volume is substantially the same as the initial volume.

17. The method for polymerizing the composition according to claim 16, wherein the change from initial volume to final volume is less than 10%.

* * * * *

UNITED STATES PATENT AND TRADEMARK OFFICE
CERTIFICATE OF CORRECTION

PATENT NO. : 8,828,542 B2
APPLICATION NO. : 12/713443
DATED : September 9, 2014
INVENTOR(S) : Choi It is certified that error appears in the above-identified patent and that said Letters Patent is hereby corrected as shown below:

On the Title Page, Item (56), under "OTHER PUBLICATIONS", in Column 2, Line 6,
delete "et al" and insert -- et al. --, therefor.

In the Specification

In Column 2, Line 25, delete "—$(CH_2)_\lambda$—O—$(CH_2)_m$;" and
insert -- —$(CH_2)_\lambda$—O—$(CH_2)_m$—; --, therefor.

In Column 11, Line 24, delete "lauryol" and insert -- lauroyl --, therefor.

In Column 14, Line 2, delete "ethylcylohexylamine," and insert -- ethylcyclohexylamine, --, therefor.

In Column 14, Lines 2 & 3, delete "methycyclohexylmethylamine," and
insert -- methylcyclohexylmethylamine, --, therefor.

In the Claims

In Column 19, Line 11, in Claim 13, delete "polymerizationreaction" and
insert -- polymerization reaction --, therefor.

In Column 19, Line 15, in Claim 14, delete "comprising;" and insert -- comprising: --, therefor.

In Column 20, Lines 4 & 5, in Claim 16, delete "moiety moieties" and insert -- moieties --, therefor.

Signed and Sealed this
Sixteenth Day of June, 2015

Michelle K. Lee
*Director of the United States Patent and Trademark Office*